US006281341B1

(12) United States Patent
Mares-Guia et al.

(10) Patent No.: US 6,281,341 B1
(45) Date of Patent: Aug. 28, 2001

(54) HETERO-POLYSACCHARIDE CONJUGATE AND METHODS OF MAKING AND USING THE SAME

(75) Inventors: Marcos Mares-Guia; Camillo Ricordi, both of Miami Beach, FL (US)

(73) Assignee: Biomm, Inc. & University of Miami, Miami, FL (US)

(*) Notice: Subject to any disclaimer, the term of this patent is extended or adjusted under 35 U.S.C. 154(b) by 0 days.

(21) Appl. No.: 08/877,682

(22) Filed: Jun. 17, 1997

Related U.S. Application Data
(60) Provisional application No. 60/045,111, filed on Apr. 30, 1997.

(51) Int. Cl.$^7$ .................... C08B 37/04; A01N 63/00; A61K 9/14

(52) U.S. Cl. .................... 536/3; 536/18.7; 536/123; 536/123.1; 536/124; 424/93.7; 424/423; 424/488; 424/493; 424/499

(58) Field of Search ............... 536/18.7, 3, 123, 536/123.1, 124; 424/93.7, 423, 488, 493, 499

(56) References Cited

U.S. PATENT DOCUMENTS

| | | | |
|---|---|---|---|
| 4,409,331 | * 10/1983 | Lim | 435/178 |
| 5,084,350 | * 1/1992 | Chang et al. | 428/402.2 |
| 5,129,877 | * 7/1992 | Gallo et al. | 600/12 |
| 5,169,631 | * 12/1992 | Rase et al. | 424/401 |
| 5,986,164 | 11/1999 | Kershaw et al. | 602/49 |

OTHER PUBLICATIONS

Aruffo, et al., (Jun. 29, 1990) "CD 44 is the Principal Cell Surface Receptor for Hyaluronate", Cell, vol. 61, pp. 1303–1313.*
Aung, et al., "Comparison of Various Gels for Immobilization of Islets in Bioartificial Pancreas Using a Mesh–reinforced Polyvinyl Alcohol Hydrogel Tune", Transplantation Proceedings, Feb. 1995, vol. 27, No. 1, pp. 619–621, see especially p. 619.*
Christenson, et al., (1993) "Biomedical Applications of Immobilized Cells", in Fundamentals of Animals Cells Encapsulation and Immobilization, pp. 7–41, month not available.*
Cole, et al., (Apr. 3, 1986) "Neuronal Cell–Cell Adhesion Depends on Interactions of N–CAM with Heparin–like Molecules", Nature, vol. 320, pp. 445–447.*
deVos, et al., (1996) "The Effect of Alginate Composition on the Biocompatibility of Alginate–polylysine Microcapsules", PhD Thesis, University of Groningen, The Netherlands, month not available.*
Goosen, (1993), Fundamentals of Animal Cell Encapsulation and Immobilization, Chapter 3, Toxicity, CRC, Press, Boca Raton, pp. 43–54, month not available.*

Hirschman, et al., (Oct. 1966) "Protein–polysaccharide loss during endochondrial ossification: immunochemical evidence", Science, vol. 154, pp. 393–395.*
Howell, et al., (1982) "Possible use of agarose gels as encapsulating media for transplantation of islets of Langerhans", J. Physiol., vol. 324, pp. 20–21, month not available.*
Jindal, et al., (Feb. 1994) "Preservation and storage of pancreatic islets", Transplantation, vol. 57, pp. 317–321.*
Johansen, et al. (1986) "A New Principle for Immobilized Yeast Reactors based on Internal Gelation of Alginate", Biotechnol Lett, vol. 8, pp. 121–126, month not available.*
LaPorte, R.J. (1997), "Hydrophilicity and the Structure of Hydrophilic Sytems",Hydrophilic Polymer Coatings for Medical Devices, Technomic Publishing Co, Inc, Lancaster Ch. 2, pp. 19–55, month not available.*
Lee, et al.,. (1994) "A Coupling Through Carbonyl Groups", Synthetic Glycoconjugates, Ch. 10, Academic Press, pp. 348–371, month not available.*
Liao, et al., (1989) "Adhesion of Lymphoid Cells to the Carboxyl–terminal Heparin–binding Domains of Fibronectin", Exp. Cell Res. vol. 181, pp. 348–361, month not available.*
Lim, et al. (Nov. 1980) "Microencapsulated islets as a bioartificial pancrease", Science, vol. 210, pp. 908–910.*
Loewi, et al., (1965) "The antigenicity of chondromucoprotein", Immunology, vol. 9, pp. 119–127, month not available.*

(List continued on next page.)

Primary Examiner—Kathleen K. Fonda
(74) Attorney, Agent, or Firm—Frommer Lawrence & Haug; Grace L. Pan (57) ABSTRACT

Disclosed and claimed are: a composition including at least one glycosaminoglycan, e.g., CIS, and at least one alginate, e.g., sodium alginate, wherein:

the at least one glycosaminoglycan and/or the alginate are cross-linked or polymerized, e.g., the alginate is cross-linked or polymerized, for instance by addition of an inorganic salt, such as a calcium salt; or the at least one glycosaminoglycan and the alginate are covalently bound, e.g., by means of a coupling reaction involving a linker molecule such as DVS; or the at least one glycosaminoglycan and/or the alginate are cross-linked or polymerized, e.g., the alginate is cross-linked or polymerized, for instance by addition of an inorganic salt, such as a calcium salt, and the at least one glycosaminoglycan and the alginate are covalently bound, e.g., by means of a coupling reaction involving a linker molecule such as DVS, and the covalent binding can have been performed prior to cross-linking or polymerizing or vice versa; and, gels comprising the composition; mixtures of such gels or of at least one such gel and at least one such composition; and, methods for making and using such compositions and gels, including products therefrom such as "paints", sprays, matrices, beads, microcapsules.

62 Claims, 5 Drawing Sheets

(3 of 5 Drawing Sheet(s) Filed in Color)

OTHER PUBLICATIONS

Magnusson, et al., (1994) "Synthesis of Neoglycoconjugates", Ch. 3, p. 53–143, in Lee and Lee (1994), *loc. Cit* month not available.*

Moscatelli, D. (Aug. 1988) "Metabolism of Receptor–bound and Matrix–bound Basic Fibroblast Growth Factor by Bovine Capillary Endothelial Cells", J. Cell. Biol., vol. 107, pp. 753–759.*

Murphy, et al. (1990) "Partial dermal regeneration is induced by biodegradable collagenglycosaminoglycan grafts", Laboratory Invest. vol. 63, pp. 305–313, month not available.*

Rodriguez et al., (Jan. 1994) "Acceleration of chronic failure of intrahepatic canine islet autografts by a short course of prednisone", Transplantation, vol. 57, pp. 181–187.*

Rosenman et al., (1993) CD–44, in Guidebook to the Extracellular Matrix and Adhesion Proteins, Oxford University Press, pp. 27–29, month not available.*

Slivka et al., (1993) "Characterization, barrier function and drug metabolism of an in vitro skin model", J. Invest. Dermatol., vol. 100, pp. 40–46, month not available.*

Stevenson et al., (1993) "Development of polyacrylate microcapsules, in Fundamentals of Animals Cell Encapsulation and Immobilization" CRC Press, Ch. 7, pp. 143–181, month not available.*

Tze et al., (1982) "Biocompatibility and immunological studies of microencapsulation with cross–linked alginate capsules", Transplantation, vol. 33, pp. 563–564, month not available.*

Wang, P.Y. (1991) "Sustained–release implants for insulin delivery, In Biotechnology of Insulin Therapy", Scientific Publications, London, pp. 42–74, month not available.*

Yannas et al., (1990) "Chemical analogs of the extracellular matrix. Cell–matrix ineractions", Polym. Mater. Sci. Eng., vol. 62, pp. 801–803, month not available.*

Young et al., (Nov./Dec. 1989) "Inverted microcarriers using microencapsulation to grow anchorage–dependent cells in suspension", Biopharm, vol. 2, pp. 34, 36, 38, 40–46.*

Zimmerman, D.R. (1993) Versican, in Guidbook to the Extracellular Matrix and Adhesion Proteins, Oxford University Press, Oxford, pp. 100–101, month not available.*

Harada et al. *J. Clin. Invest.* Aug. 1994, 94, 623–630.*

Murata et al. *Journal of Controlled Release* 1996, 38, 101–108, month not available.*

Yuan et al. *Proceed. Intern. Symp. Control. Rel. Bioact. Mater.* 1996, 23, 238–239, month not available.*

Aung et al. *Transplantation Proceedings* Feb. 1995, 27(1), 619–621.*

Schmidt et al. *J. Pharm. Pharmacol.* 1993, 45, 508–513, month not available.*

* cited by examiner

Biodritin Spaghetti with cotton line structure

FIG. 2B

BIODRITIN GEL CYLINDERS TIED IN A BUNDLE.

HETERO-POLYSACCHARIDE CONJUGATE AND METHODS OF MAKING AND USING THE SAME

CROSS-REFERENCE TO RELATED APPLICATIONS

Reference is made to copending U.S. application Ser. No. 08/417,652, filed Apr. 5, 1995, incorporated herein by reference. Reference is also made to U.S. provisional application Ser. No. 60/045,111, filed Apr. 30, 1997 (Attorney Docket No. 540519-2004), incorporated herein by reference.

FIELD OF THE INVENTION

This invention relates to: a novel hetero-polysaccharide conjugate or complex, gels therefrom and/or a composition, e.g., solutions having adjustable viscosity, prepared by manipulating the concentration of hetero-polysaccharide conjugate or complex, and/or ion concentrations, e.g., calcium; and/or a gel or sol comprising the hetero-polysaccharide conjugate; the synthesis, purification and utilization of a novel glycopolymer and/or hetero-polysaccharide and/or gels, solutions and/or sols; and especially, a neo-heteropolysaccharide conjugate or complex, herein referred to as "Biodritin heteropolysaccharide", comprising a heteropolysaccharide from covalent bonding between at least one glycosaminoglycan, e.g., chondroitin sulfate-4 and/or 6, and at least one alginic acid salt, e.g., sodium alginate, preferably via a coupling reaction via a linking molecule such as divinyl sulfone.

Thus, the invention especially relates to Biodritin heteropolysaccharide, gels therefrom and/or a composition, e.g., solutions having adjustable viscosity, prepared by manipulating the concentration of Biodritin heteropolysaccharide, and/or ion concentrations, e.g., calcium; and/or a gel or sol comprising the Biodritin heteropolysaccharide; the synthesis, purification and utilization of Biodritin heteropolysaccharide as a novel glycopolymer and/or heteropolysaccharide and/or gels, solutions and/or sols comprising Biodritin heteropolysaccharide. Gels are obtained by adding an inorganic ion, such as calcium ions, to Biodritin heteropolysaccharide. Sols can be obtained by treatment of a gel with a suitable agent such as a sodium salt, e.g., citrate salts or ethylene-diamine-tetraacetic (EDTA) as sodium salt. Gels can have varying viscosity by varying the amount of Biodritin heteropolysaccharide and/or inorganic ion, e.g., calcium ion; and with an amount of calcium ions, infinite gels can be obtained.

The invention further relates to a composition herein termed "Biodritin polymer network", and to methods and formulations for preparing a Biodritin polymer network. A Biodritin polymer network comprises at least one glycosaminoglycan, e.g., chondroitin sulfate-4 and/or 6, and at least one alginic acid salt, e.g., sodium alginate, wherein at least one of the glycosaminoglycan and alginic acid salt is cross-linked. And, the methods and formulations for preparing a Biodritin polymer network comprises admixing the glycosaminoglycan and alginic acid salt and adding at least one cross-linking agent, e.g., an inorganic ion. For instance, a Biodritin polymer network which is believed, without necessarily wishing to be bound by any one particular theory, to be a semi-interpenetrating polymer network (s-IPN), is formed by addition of inorganic ions to a solution of a glycosaminoglycan and an alginic acid salt, e.g., calcium ions added to a solution of chondroitin sulfate-4 and/or -6 and sodium alginate (wherein sodium alginate is cross linked and has pockets of chondroitin sulfate-4 and/or -6 and/or non-cross-linked sodium alginate).

Of course, a Biodritin polymer network containing at least one Bioditrin heteropolysaccharide can be obtained by covalently bonding the glycosaminoglycan and alginic acid salt present in a Biodritin polymer network, e.g., subjecting a Biodritin polymer network to a coupling reaction involving a linker molecule; for instance, forming network by addition of inorganic ions to a solution of a glycosaminoglycan and an alginic acid salt, e.g., calcium ions added to a solution of chondroitin sulfate-4 and/or -6 and sodium alginate, and subjecting network to coupling reaction, e.g., subjecting network to coupling reaction involving divinyl sulfone.

In preparing a Biodritin heteropolysaccharide or Biodritin polymer network comprising a Biodritin heteropolysaccharide, a solution of GAG, e.g., chondroitin sulfate-4 and/or -6 is linked to alginate, e.g., sodium alginate by covalent bonding via reaction with a linker molecule such as divinyl sulfone; the reaction is preferably in alkaline medium. In practicing the invention, one can employ a process to protect the calcium binding sites of alginate, also known as "egg-box" sites, such that no reaction occurs to these sites during the linking reaction with the linker molecule, e.g., divinyl sulfone, and GAG, e.g., chondroitin sulfate. One can also employ a process to eliminate remaining active vinyl groups in Biodritin, after linking, by reaction with an alkanolamine such as ethanolamine, preferably at alkaline pH. And, one can employ a process to purify Biodritin after the synthesis reaction which involves removal of calcium with molecule which binds to or conjugates with calcium, e.g., EDTA, preferably followed by precipitation(s) with an alchol such as ethanol.

The invention also relates to an additional process to prepare a Biodritin polymer network comprising dehydrothermal cross-linking of a mixture of the polymers that form a Biodritin heteropolysaccharide. The dehydrothermal reaction can be of a dry cake containing GAG, e.g., chondroitin sulfate and alginate, e.g., sodium alginate. The cake can be produced by freeze-drying a solution containing chondroitin sulfate and sodium alginate in proper concentrations. The calcium binding sites of alginate can be protected prior to the dehydrothermal treatment by adding calcium ions to bind to the "egg-box" sites of alginate. The calcium can be removed from the "egg-box" complexes by treatment of the dehydrothermal reaction product with a material which complexes or conjugates or binds with calcium, e.g., sodium EDTA. Purification can be as discussed above.

For ease of reference, Biodritin polymer networks and Biodritin heteropolysaccharides may be termed "Biodritin" or "Biodritin products".

A primary use of Biodritin products and/or products derived therefrom is in applications where biocompatibility with host tissues and/or immunoisolation are issues, for example, in cell encapsulation, such as immunoisolation by microencapsulation of islets of Langerhans for diabetes control, or of other cells types or tissues. A Biodritin gel formed from Biodritin heteropolysaccharide or comprised of a Biodritin polymer network (e.g., a gel comprising at least one glycosaminoglycan, e.g., chondroitin-4 and/or -6 and at least one alginic acid salt wherein at least one of the glycosaminoglycan and alginic acid salt are cross-linked and the gycosaminoglycan and alginic acid salt are optionally (and preferably) covalently bound, preferably via a reaction involving a linker molecule such as divinyl sulfone, and the cross-linking can be performed after the covalent binding or prior thereto; generally, a Biodritin product or a product from reaction with Biodritin) can be used to form beads or microcapsules containing cells or tissues for implantation. And thus, the invention relates to such beads or microcapsules, and methods for making and using such beads or microcapsules.

Biodritin products and/or products therefrom can also be "painted", sprayed or applied to or on top of wounds, e.g., surgical wounds or sutures, and can be used to coat surgical, monitoring, or other equipment to avoid local reaction, injury or irritation. The skilled artisan can apply such without undue experimentation considering the disclosure herein and the knowledge in the art, and typical factors such as the age, sex, weight, condition of the patient, etc. or the nature of the equipment to be coated. Biodritin products and/or products therefrom serves as a matrix material for supporting cells for culturing or other applications in which cells must maintain a suspended or non-aggregated state. Accordingly, the invention relates to "paints", sprays, and matrices comprising Biodritin products and/or products therefrom, and to methods for making and using them.

The novel heteropolysaccharide and products therefrom, as well as the semi-interpenetrating polymer network, i.e., Biodritin heteropolysaccharide and products therefrom and the Biodritin polymer network, make use of: the biocompatibility of glycosaminoglycans (GAGs), preferably of a specific group of glycosaminoglycans, namely those which do not have defined cell binding properties, preferably chondroitin sulfates-4 and/or -6, herein referred to as CIS; and the desirable properties of algal polysaccharides and/or alginic acid, preferably in the form of a salt of alginic acid, e.g. M+ alginate-, wherein M is a cation, such as a metal cation, which serves as a stoichiometric counterion to balance negative charges of the alginate anion, e.g., a Group I metal, such as sodium, lithium, or other cations, e.g., organic and complex cations, e.g., ammonium. Preferably, the counterion is sodium and the salt of alginic acid is sodium alginate, which is able to form infinite gel networks in the presence of calcium ions.

Chondroitin sulfates-4 and -6 are preferred as they are able to impart biocompatibility due to the following characteristics: their ubiquity in animal tissues, as components of the extra-cellular matrix or linked to proteins on cell surfaces; their lack of immunogenicity; and their apparent inability to bind specifically to known receptors or cell types. These properties, coupled with covalent bond formation, and the gel-forming properties of salts of alginic acid, forms a basis for the present invention. Although alginate is used in cell and tissue encapsulation studies, there is considerable discussion as to the extent of its biocompatibility (devos et al., 1996). The present invention overcomes these obstacles by joining together alginate and CIS, through stable chemical bonds, or in physical gels, e.g., semi-interpenetrating polymer networks, in such a way that the desired properties of each could be preserved and become useful.

Thus, broadly the invention relates to a heteropolysaccharide, preferably from covalent bonding between at least one glycosaminoglycan, e.g., chondroitin sulfate-4 and/or -6, and at least one alginate or alginic acid salt, e.g., one that forms gels, such as infinite gels in the presence of calcium ions, for instance, sodium alginate, preferably via a coupling reaction with a linking molecule, e.g., DVS.

The invention additionally relates to a formulation comprising at least one alginate and glycosaminoglycan, e.g., chondroitin sulfate-4 and/or -6 mixed together in solution and polymerized or cross-linked to form a physical gel or polymer network by addition of a polymerizing or cross-linking agent, e.g., calcium ions; e.g, a gel or polymer network which is a semi-interpenetrating polymer network. Thus, the invention relates to a formulation comprising a gel or polymer network from polymerizing or cross-linking a mixture comprising at least one alginate and at least one glycosaminoglycan; for instance, a formulation comprising a gel or polymer network from adding calcium ions to a mixture comprising at least one alginate and at least one glycosaminoglycan.

The invention also relates to a formulation comprising a gel from covalently bonding and cross-linking or polymerizing a mixture comprising at least one alginate and at least one glycosaminoglycan; for instance, a gel from adding calcium ions to the inventive heteropolysaccharide, or a gel from subjecting an inventive gel or polymer network to a coupling reaction such as a coupling reaction involving a linker molecule such as DVS. The latter type of gel has a stabilized network, due to the linkages by covalent bonding via the linker molecule and the cross-linking or polymerizing prior thereto.

The invention further relates to a formulation comprising a combination (mixture) of the inventive heteropolysaccharide and/or gel therefrom and an inventive formulation or a mixture of inventive formulations, e.g., a mixture of inventive gels, described above.

Therefore, the invention, even more broadly, relates to:
a composition comprising at least one glycosaminoglycan and at least one alginate, wherein:
the at least one glycosaminoglycan and/or the alginate are cross-linked or polymerized, e.g., the alginate is cross-linked or polymerized, for instance by addition of an inorganic salt, such as a calcium salt; or
the at least one glycosaminoglycan and the alginate are covalently bound, e.g., by means of a coupling reaction involving a linker molecule such as DVS; or
the at least one glycosaminoglycan and/or the alginate are cross-linked or polymerized, e.g., the alginate is cross-linked or polymerized, for instance by addition of an inorganic salt, such as a calcium salt, and the at least one glycosaminoglycan and the alginate are covalently bound, e.g., by means of a coupling reaction involving a linker molecule such as DVS, and the covalent binding can have been performed prior to cross-linking or polymerizing or vice versa; and,
gels comprising the composition; mixtures of such gels or of at least one such gel and at least one such composition; and,
methods for making such compositions and gels; and
methods for using such compositions and gels, including as "paints", sprays, matrices, beads, microcapsules; and,
products comprising the composition or gel, e.g., "paints", sprays, matrices, beads, microcapsules.

A Biodritin heteropolysaccharide solution is transformed into gel microcapsules by dripping the solution into a calcium chloride solution. A Biodritin heteropolysaccharide solution is fashioned into a slab of any desired shape by contacting the Bioditrin heteropolysaccharide and calcium chloride solution and thus gelling the Biodritin in the forms of the desired shape, such that the shape of the gel may be varied, as desired. The gel microcapsules or slab can have pancreas islets of Langerhans therein.

Biodritin can also be formed into a "spaghetti"-like structure, prepared by extrusion of a Biodritin heteropolysaccharide solution over a line, e.g., through a cylindrical catheter tube containing inside a cotton or surgical line. The biodritin solution is extruded together with the line into a calcium ion containing solution, whereby a gel instantly forms that contains the line. The gel is then matured in a calcium ion solution. One can form a protective outer layer, e.g., of poly-lysine/Biodritin, over the Biodritin spaghetti, to provide limited permeability to the device. The structuring of the spaghetti device is by the line in the interior and extending further out therefrom towards the surrounding gel cylinder, e.g., by the lateral extensions of the line, or by those provoked on the surface of the line by scraping it, e.g., with a knife blade.

A Biodritin spaghetti string can be used for implantation of cells or tissues therein contained, e.g., from the lateral extensions; or more than one Biodritin spaghetti strings may be used by being tied up together at each end. The strings can be further inserted within a biocompatible material such that the biodritin spaghetti strings are protected from mechanical strains after implantation. And, these string devices can be used as a means of implanting cells or tissues in humans and animals for disease prevention or treatment, as is the case of islets of Langerhans implants for diabetes treatment.

The skilled artisan can implant a composition containing cells, such as islet cells, without undue experimentation, taking into account typical factors such as the age, sex, condition etc. of the patient, and the rate of secretion of a desired expression product of the cells, e.g., insulin (see also U.S. Ser. No. 08/417,652, filed Apr. 5, 1995, now U.S. Pat. No. 5,808,050, incorporated herein by reference).

Thus, the invention relates to these products and methods for preparing and using them.

Analogous methods can be used to prepare products from Biodritin polymer networks; and, the invention accordingly relates to these products and methods for preparing and using them.

With respect to glycosaminoglycans, such as heparan sulfate, heparin and hyaluronic acid, these are not preferred for the invention as they can have defined cell binding properties. With respect to material having defined cell binding properties which renders them unsuitable for use in the instant invention, hyaluronic acid binds specifically to CD-44, also known as "lymphocyte homing receptor" (Hermes-antigen) or "major hyaluronic acid receptor of mammalian cells" (Aruffo et al, 1990). CD-44 is expressed on the surfaces of most mammalian cells, rodent and primate hematopoietic cell types, fibroblastoid, neural and muscle cells (Rosenmann and St.John, 1993). Hyaluronic acid also binds to Versican, a large proteoglycan secreted by fibroblasts that promotes cell adhesion through interactions with components of the extracellular matrix and cell surface glycoproteins (Zimmermann, 1993).

Further, as to the use of materials having undesirable defined cell binding properties, heparin is also not preferred to be linked to alginate in the composition due to its well known inhibition of the blood clotting mechanism. Heparan sulfate is also not preferred on the basis of its participation in cell-cell adhesion mechanisms. Heparan sulfate is linked to a membrane-bound proteoglycan that binds NCAM (neural cell adhesion molecule), thereby promoting homophilic cell adhesion(Cole et al, 1986). The heparan sulfate binding domain of fibronectin is responsible for the binding of neurons, lymphocytes and other cell types to fibronectin, in the process of cell-cell adhesion (Liao etal, 1988). Further, heparan sulfate proteoglycans found on cell surfaces and in the extracellular matrix are binding sites for the basic fibroblast growth factor(bFGF) (Moscatelli et al, 1988).

Thus, having established that CIS is the most desirable glycosaminoglycan to utilize for the purposes of the present invention, the inventive heteropolysaccharides arise from stable, covalent chemical bonds between the structures of the at least one alginic acid salt, e.g., sodium alginate and the at least one glycosaminoglycan, e.g., CIS, for example, by a coupling reaction with divinyl sulfone, DVS. These reactants can produce a novel neo-hetero-polysaccharide conjugate having desired properties for use in cell and tissue biology, whenever biocompatibility and/or immunoisolation are critical issues. Along the same line, a semi-interpenetrating polymer network can be prepared by mixing CIS and alginate, at desired concentrations and forming a gel by addition of calcium ions that has similar properties to and benefits of the inventive heteropolysaccharides.

Thus, the invention can relate at least to two processes.

First, the present invention provides a process for preparing a heteropolysaccharide comprising covalently bonding at least one glycosaminoglycan, e.g., CIS, and at least one alginic acid salt, e.g., sodium alginate, preferably by a coupling reaction with a linker molecule, e.g., DVS, such that the calcium binding sites in alginate are preserved and/or conserved during the coupling reaction. These sites provide the flexibility of using the hetereopolysaccharide as a sol or a gel of desired strength, or as a composition having adjustable viscosity; and, the present invention relates such products from the heteropolysaccharide and to method for making and using them, e.g, by contacting with ions, such as calcium ions to prepare a gel, for instance, an infinite gel.

The second process forms a physical gel, e.g., of the semi-interpenetrating polymer network type, by addition of a polymerizing or cross-linking agent, e.g., calcium ions to a solution containing both at least one alginate and at least one glycosaminoglycan, e.g., chondroitin sulfate-4 and/or -6. This gel can be a composition that can be varied to suit specific applications. The inventive s-IPN gel is stable and is formed by the complexation of calcium ions with poly-guluronic blocks of alginate to form the "egg-box" structures that stabilize the gel.

Still, further within the principles just delineated, another formulation can be prepared by suitable combination of the formulations described above, in which a given amount of the covalently bound heteropolysaccharide conjugate is mixed in solution with alginate and CIS, to which solution calcium ions are added to form the gel.

Likewise, another formulation can be prepared by subjecting an inventive gel to a linking reaction so as to covalently bond glycosaminoglycan and alginate units to each other, e.g., by subjecting the gel to a coupling reaction involving a linker molecule such as DVS.

The invention further relates to uses of gels and compositions which can be formed into gels, especially biocompatible gels, such as in "paints", sprays, matrices, beads, microcapsules, and the like, including novel uses such as "spaghetti"-like material comprising a spine, e.g., a suture or thread, having a desired material connected thereto, e.g., cells connected to the spine, and an inventive gel surrounding the spine, e.g., in a cylindrical manner.

Documents are cited in this disclosure with a full citation for each appearing thereat. These documents relate to the state-of-the-art to which this invention pertains, and each document cited herein is hereby incorporated by reference.

BACKGROUND OF THE INVENTION

Cells and tissues may be immobilized and immunoisolated by three basic techniques: in extravascular chambers isolated but in the path of the blood stream, in spherical dispersions or microcapsules, and within macrocapsules. Using these techniques a great variety of cells and tissues of different animals have been immunoisolated and implanted in animals for development of therapeutic systems (reviewed by Christenson et al (1993)). Indeed, future applications of immunoisolated cell therapy are envisaged for diseases or conditions such as diabetes, hemophilia, hepatic failure, Alzheimer's, Parkinson's and Huntington's diseases, affective disorders, hepatic failure and fertility problems (Christenson et al, 1993). A complete review of the questions involved in encapsulation and immunoisolation is presented in a recent volume edited by Goosen (1993).

In the case of diabetes mellitus, alternatives to daily insulin injections have been searched for control of type I diabetes, or insulin-dependent diabetes mellitus (IDDM). These included pancreas transplants, pumps to deliver insulin under a controlled program and, more recently, Langerhans' islets transplantation. A review of sustained-release implants for insulin delivery has been published (Wang, 1991).

Several researchers have proposed different approaches to protect islet tissue from host attack after transplantation; these include encapsulation of islets in different materials such that insulin may be secreted but the beta-cells in the islet tissue will be immunologically isolated from the host. Polysaccharides have been proposed to form membranes, as is the case of agarose, by Howell et al(1982) or alginate, by Tze and Tai (1982). Materials used include synthetic polyacids and polybases, gelatin and polyamino acids (Young et al, 1989) as well as different polysaccharides: chemically modified dextran, to form poly-ionically bonded capsules (Lim and Hall, 1988, PCT Int. Appl. WO 8,800,327), entrapment in alginate followed by stabilization with poly-lysine and alginate (Chang and Wong, 1992, U.S. Pat. No. 5,084,350), as well as a combination of chitosan and carboxy-methyl cellulose to form capsules of controlled permeability (Shioya and Hirano, 1990, U.S. Pat. No. 5,089, 272).

Additionally, recent work bearing on regeneration of skin in culture has pointed out the important role of GAG's in the process, in studies where mixtures of collagen and GAG were used as support (Murphy et al, 1990; Yannas et al, 1990). Along the same line, keratinocytes and fibroblasts grown on a nylon mesh produced a dermal-like matrix containing proteoglycans (Slivka et al, 1993).

The importance of the extra-cellular matrix components for the normal development of the skin system lends support to a basis of the instant invention, e.g., that foreign molecules combined or structured with specified GAG's, e.g., preferably CIS in the case of this invention, will constitute ideal protecting materials in transplantation or implantation of cells or tissues of human or animal origin, with the purpose of treating or controlling disease However, the art heretofore fails to teach or suggest the particular heteropolysaccharides polymer networks, and products therefrom and processes and uses of the invention.

Further, essential constituents of the extra-cellular matrix in connective tissues, of cell membranes and endothelial lining, and the overall presence of GAG's demonstrates their importance in matrix formation and extension, and in cell-matrix and cell-cell interactions. Although GAG's occur in an organism mostly linked to proteins, as proteoglycans, it has been demonstrated that only the protein portion is immunogenic; the glycosaminoglycan, e.g., CIS component, is not immunogenic by itself (Hirschmann and Dziewiatkowski, 1966; Loewi and Muir, 1965).

However, use of a GAG with an alginate salt, for instance GAG-alginate biomolecules, e.g., via a coupling reaction with a linker molecule, to form a heteropolysaccharide conjugate and products therefrom and processes and uses of the invention, are not heretofore taught or suggested. Moreover, the formation of a polymer network, e.g., of a semi-interpenetrating polymer network, based on the two components, alginate and GAG, e.g., CIS, rendered in gel form by addition of ions such as inorganic ions, e.g., calcium ions, has not been taught nor suggested in the prior art. Nor has a polymer network comprising a heteropolysaccharide from coupling GAG-alginate present in a GAG-alginate polymer network, been heretofore taught or suggested.

In the case of diabetes, the depth of interest in discovering the best way to use islets in transplantation is demonstrated by two recently published papers, one dealing with storage and preservation of islets (Jindal and Gray, 1994) and the other with the action of prednisone on the islet autograft function (Rodrigues Rilo et al, 1994).

U.S. Pat. No. 4,409,331 to Lim relates to the encapsulation of islets in polymeric material formed from alginate and poly-lysine; Lim and Sun (1980) discussed the microencapsulation of islets to form a bioartificial pancreas. Chitosan microspheres were developed that bind to GAG receptors on cell surfaces (Gallo et al U.S. Pat. No. 5,129,877). Collagen-GAG microcapsules were proposed as drug delivery systems, to deliver anti-microbial agents (Rase et al U.S. Pat. No. 5,169,631). Polyacrylates were also developed as encapsulation materials and have also been co-polymerized with alginate, as discussed by Stevenson and Sefton (1993). However, use of GAG with an alginate salt, GAG-alginate biomolecules, e.g., in physical mixture or bound via a coupling reaction with a linker molecule, to form a heteropolysaccharide or a physical network, e.g., s-IPN, gel and products therefrom and processes and uses of the invention, are not taught or suggested.

It is emphasized, however, that none of the art heretofore has GAG acted as the major biocompatibility agent between a foreign chemical structure or device and host organism, especially in a composition with an alginate.

The synthesis and properties of glycoconjugates has been reviewed in a book edited by Lee and Lee (1994). The new class of structures now being described herein belongs to a group of glycopolymers formed by joining together two different natural heteropolysaccharides by reaction with an unnatural tether.e.g., divinyl sulfone. This new class would enter the list of neoglycoconjugates compiled by Magnusson et al(1994) under the heading "glycopolymers with gel forming properties".

On the other hand, the physical gel formed by adding calcium ions to solutions containing variable concentrations of GAG, e.g., CIS, and alginate belongs to the group of polymers known as semi-interpenetrating polymer networks, recently discussed by LaPorte (1997). In this category, one type of polymer is enmeshed and entrapped by a second polymer, which is cross-linked to stabilize the structure.

However, that compositions of the invention may be characterized as "glycopolymers with gel forming properties" or as a "polymer network", e.g., "a semi-interpenetrating polymer network" does not mean that the invention has heretofore been taught or suggested.

SUMMARY OP THE INVENTION

Thus, the present invention provides a novel hetero-polysaccharide conjugate or complex, gels and/or sols derived therefrom, and to the synthesis, purification and utilization of a novel glycopolymer and/or heteropolysaccharide and/or gels, solutions and/or sols, herein referred to as biodritin. The inventive hetero-polysaccharide is preferably formed from covalent bonding between at least one glycosaminoglycan, e.g., chondroitin sulfate-4 and/or -6, and at least one alginic acid salt, e.g., such that a gel and/or sol is formed, e.g., in the presence of an appropriate counterion, e.g., calcium.

An additional formulation of the invention combines the two polysaccharides, alginate and GAG, e.g., CIS, in aqueous solutions having variable concentrations of either component, through the formation of a gel of the type semi-interpenetrating polymer network, by addition of a cross-linking or polymerizing agent, e.g., calcium ions. A third formulation combines the two concepts in the same preparation, in suitable proportion, which can be established by the skilled artisan, without undue experimentation, from this diclosure and the knowledge in the art.

Therefore, the invention, provides:

a composition comprising at least one glycosaminoglycan, e.g., CIS, and at least one alginate, e.g., sodium alginate, wherein:

the at least one glycosaminoglycan and/or the alginate are cross-linked or polymerized, e.g., the alginate is cross-linked or polymerized, for instance by addition of an inorganic salt, such as a calcium salt; or the at least one glycosaminoglycan and the alginate are covalently bound, e.g., by means of a coupling reaction involving a linker molecule such as DVS; or the at least one glycosaminoglycan and/or the alginate are cross-linked or polymerized, e.g., the alginate is cross-linked or polymerized, for instance by addition of an inorganic salt, such as a calcium salt, and the at least one glycosaminoglycan and the alginate are covalently bound, e.g., by means of a coupling reaction involving a linker molecule such as DVS, and the covalent binding can have been performed prior to cross-linking or polymerizing or vice versa; and, gels comprising the composition; mixtures of such gels or of at least one such gel and at least one such composition; and, methods for making such compositions and gels; and methods for using such compositions and gels, including as "paints", sprays, matrices, beads, microcapsules; and, products comprising the composition or gel, e.g., "paints", sprays, matrices, beads, microcapsules.

The inventive composition can be obtained by admixing 0.5% to 5.0%, e.g., 1% to 3%, by weight or by volume of alginate, e.g., sodium alginate, and about 1.0%, e.g., 1.5% or 2.0%, to up to 20% to 30%, e.g., 25%, by weight or by volume of GAG, e.g., CIS. That is, in general, in forming inventive compositions the alginate to GAG ratio can be 0.5:30; but, preferably three (3) to four (4) times more GAG is present than alginate (by weight or by volume), i.e., a preferred alginate to GAG ratio in forming inventive compositions is 1:3 to 1:4. Alginates come in varying viscosities, e.g., high viscosity, medium viscosity. Medium viscosity alginates are preferred as high viscosity alginates can result in harder beads. Further, the amount of alginate employed in forming an inventive composition can be limited by the viscosity of the alginate; with a medium viscosity alginate, 5% by weight or volume alginate is rather viscous. Furthermore, the skilled artisan can readily appreciate that the volume and viscosity or hardness of compositions, gels and products therefrom, e.g., beads, etc. can be varied without undue experimentation by varying the amount of GAG, e.g., CIS and alginate, e.g., sodium alginate. For instance, when a softer composition, gel or product, having more volume, is desired, more GAG is employed, i.e., the amount of GAG by weight or volume is increased; and, when physical resistance, hardness, and like properties are desired, more alginate is employed, i.e., the amount of alginate by weight or volume is increased.

When a linker molecule is used in forming an inventive compound, it can be used in an amount relative to the amount of alginate, or to the amount of GAG present, e.g., an amount from 50% of to equal by weight, volume or stoichiometrically to the amount of alginate present, or to the amount of GAG present, or twice or thrice the weight, volume or stoichiometric amount of alginate or GAG present. When an inorganic ion is used as a cross-linking or polymerizing agent in forming a composition of the invention, the inorganic ion is preferably a calcium ion, e.g., calcium chloride, which can be used in an amount relative to the amount of alginate present, e.g., in an amount of about 0.05% to 2.0% by weight or by volume, e.g., about 1.0% by weight or by volume.

Gels can be essentially covalent, or part covalent and part interpenetrating. From analysis of inventive gels, e.g., HPLC analysis showing bands corresponding to alginate, CIS and a covalent structure, it is believed that gels of the invention form interpenetrating networks. However, Applicants do not necessarily wish to be bound by any one particular theory.

Biodritin can be applied to surgical wounds or sutures, to protect from adherences; it also serves as a matrix material for supporting cells for culturing or other applications in which cells must maintain a suspended or non-aggregated state.

These and other embodiments will be described and/or will be obvious from the following detailed description.

BRIEF DESCRIPTION OF THE FIGURES

The file of this patent contains at least one drawing executed in color. Copies of this patent with color drawing(s) will be provided by the Patent and trademark Office upon request and payment of the necessary fee.

DETAILED DESCRIPTION

Without wishing to necessarily limit the foregoing, the following shall discuss the invention with respect to certain preferred embodiments. It has now been found that the chemical polymerization of an algal polysaccharide, alginic acid, under the form of sodium alginate, with a specific group of animal heteropolysaccharides, e.g., chondroitin sulfate-4 and -6, CIS, results in new materials, e.g., Biodritins, that can be classified as neo-heteropolysaccharide conjugates having novel properties in relation to the parent molecules, while preserving most of the chemical characteristics of both parent molecules. The general properties of this new class of compounds include any or all, and preferably all of Biodritins are polyanions, carrying both carboxylate and sulfate groups (alginate contains carboxylates, while chondroitin sulfate contains both carboxylates and sulfates); Biodritins form infinite gels when treated with calcium ion, a property imparted by the alginate moiety. Biodritins dissolve readily in water. Additionally, the viscosity of the solutions can be regulated by adjusting the concentration of Biodritin, as well as the concentration of calcium.

Biodritins can also be prepared by polymerization of CIS and alginate, in mixed solutions, by addition of calcium ions, thereby resulting in the formation of stable gels of semi-interpenetrating polymer network, in which the CIS component is entrapped in the gel network formed by calcium alginate.

By adding calcium in sufficient concentration, Biodritins form stable gels, as the synthesis process of the invention was designed to preserve, with extreme care, the calcium binding sites in the alginate component. The presence of the chondroitin sulfate component, on the other hand, imparts a stronger negative charge of sulfates and similarity to an extracellular matrix to Biodritins, rendering them entirely biocompatible for applications in transplantation of cells and tissues, among others.

Biodritin-derived materials can have their permeability barrier controlled by ionic complexation with positively charged polymers such as poly-L-lysine or poly-L ornitine, which form a thin external capsule to the gel. The pore size of this capsule can be adjusted as desired, by changing the concentration and molecular weight of the positively charged polymer during capsule formation.

In the synthesis of the invention compositions, Biodritin preferably has a GAG content ranging from 2 to 200% of the alginate composition by weight, depending on the specific reaction conditions. The final composition can be adjusted by combining Biodritin that has been cross-linked with Biodritin formed by the gelling of alginate and CIS, in the same solution. Within this range, the compounds have the desired properties for use as transplantation materials. Insoluble materials can also be prepared by controlling the polymerization conditions. These may have utility as fillers in tissue repair, or as surfaces to allow cell growth in culture.

The surface of Biodritin beads exposed to an aqueous solvent carries the functionalities of both alginate and chondroitin sulfate (GAG) carboxylates, sulfates, hydroxyls, as well as glycosidic links and the sulfone group of the cross-linker moiety; the negatively charged sulfate and carboxylate groups are able to form strong ion-ion complexes with polycations such as poly-lysine or poly-ornithine, thereby providing additional external structure and protection to the beads, which has been observed for alginate capsules. These complexes formed at the outer surface of the microcapsules also help to define pore sizes.

The viscous solutions obtained by dissolving Biodritin in water or saline or other desired aqueous medium are easily handled, especially if the concentration is kept under 4% (w/v) and that they are not exposed to calcium ions. Such solutions can be transformed into infinite gels by complexation with calcium ions; e.g., by dripping them from syringes or capillaries into solutions of calcium chloride one obtains microbeads of desired spherical size. Further treatment with positively charged molecules such as poly-lysine results in a thin external capsule that may, again, be protected by layering Biodritin on top of it from a dilute solution.

A Biodritin solution can be extruded, e.g., from a thin tubing directly into a calcium chloride solution, whereby a gel in the form of a rod or cylinder of uniform diameter is obtained. Cells or tissues can be held within these cylinders for the purposes of culturing or transplantation.

The biodritin gel may also be conformed, e.g., as a slab of desired size and shape where cells or tissues may become entrapped, for purposes of culturing or implantation.

Another use of biodritin is in the protection of recent sutures: a biodritin sol may be "painted" or applied directly with a sterile brush or sprayed around the suture area, followed by spraying with an appropriate calcium chloride solution. A soft, protecting gel forms immediately around the suture area, protecting it from invading cells by blocking cell adhesion. Biodritin gel itself can be sprayed, painted or applied on a suture to protect it from adherences. The skilled artisan can determine the suitable viscosity of the gel and the amount thereof to employ to spray, paint or apply, without undue experimentation, from the knowledge in the art, the disclosure herein, and typical factors such as the wound or suture, and the condition of the patient.

The chemical coupling of the two major biodritin components, preferably, sodium alginate and chondroitin sulfate-4 and/or -6 is carried out by reaction with a linker molecule, e.g., divinyl sulfone, abbreviated DVS. A linker molecule is a small molecule that is very susceptible to nucleophilic attack (see U.S. Ser. No. 08/417,652, incorporated herein by reference, with respect to other types of linker molecules and types of coupling reactions). The reaction is carried out at alkaline pH, under conditions which allow the calcium binding sites in alginate to be protected from reaction. The final product of the cross-linking reaction is then rendered soluble and can be separated from the reagents through purification by repeated alcohol precipitation.

The concentration of linker molecule, e.g., DVS, used in the reaction can define the final solubility of the glycopolymer complex; beyond a certain range insoluble materials are formed.

An alternative to the chemical coupling of CIS and alginate is the preparation of biodritin by formation of a physical gel from a solution containing both polymers, in desired concentrations. This gel forms when calcium ions are added, and the resulting gel is of the semi-interpenetrating polymer network type, s-IPN. In this type of polymeric gel, the cross-linked structure is derived from only one component, e.g. alginate, by the formation of the "egg-box" structures resulting from the binding of calcium ions to poly-guluronic blocks in alginate. The resulting gel network entraps and holds the CIS chains that are intertwined with alginate, such that CIS molecules remain as components of the gel structure, imparting to that gel structure the properties of CIS.

An element of the invention is the ability of the final product, Biodritin, to form gels with calcium ions. This is achieved by protecting the calcium binding sites in alginate, also called "egg-box" sites, from reacting with the cross-linking reagent during the synthesis of the chemically coupled variant of Biodritin. This is accomplished by adding the appropriate amount of calcium ions to the alginate solution prior to the coupling reaction in such a way that the calcium-"egg-box" complexes are pre-formed, while avoiding strong gelling, and the solution co-polymerization reaction is not blocked.

Early in the purification steps of the final product the protecting calcium ions are removed from the "egg-box" complexes, allowing for the dissolution of the particles to form a viscous solution that can, then, be treated as desired.

The ability of the inventive compositions to easily and rapidly go from solution to gel and from gel to solution, by manipulation of the calcium ion concentration, is another significant property of the invention, as it leads to additional applications of this new material outside the transplantation field.

In another embodiment of the present invention, the chemical combination of alginate, e.g., sodium alginate and GAG, e.g., chondroitin sulfate-4 and/or -6 is made by dehydrothermal reaction, at temperatures of about 100° C. In this case, DVS is not used and ester bonds are formed between the alcoholic hydroxyls and acidic groups in alginate and chondroitin sulfate. Also using DHT, protection of the "egg-box" sites is obtained, and this is useful for preservation of the gelling properties of Biodritin.

It is emphasized that, given the purification steps after reaction, commercially available reactants have been used in all tests herein without preliminary purification, and with no negative effects on the properties of the final product, Biodritin.

Figure 1:
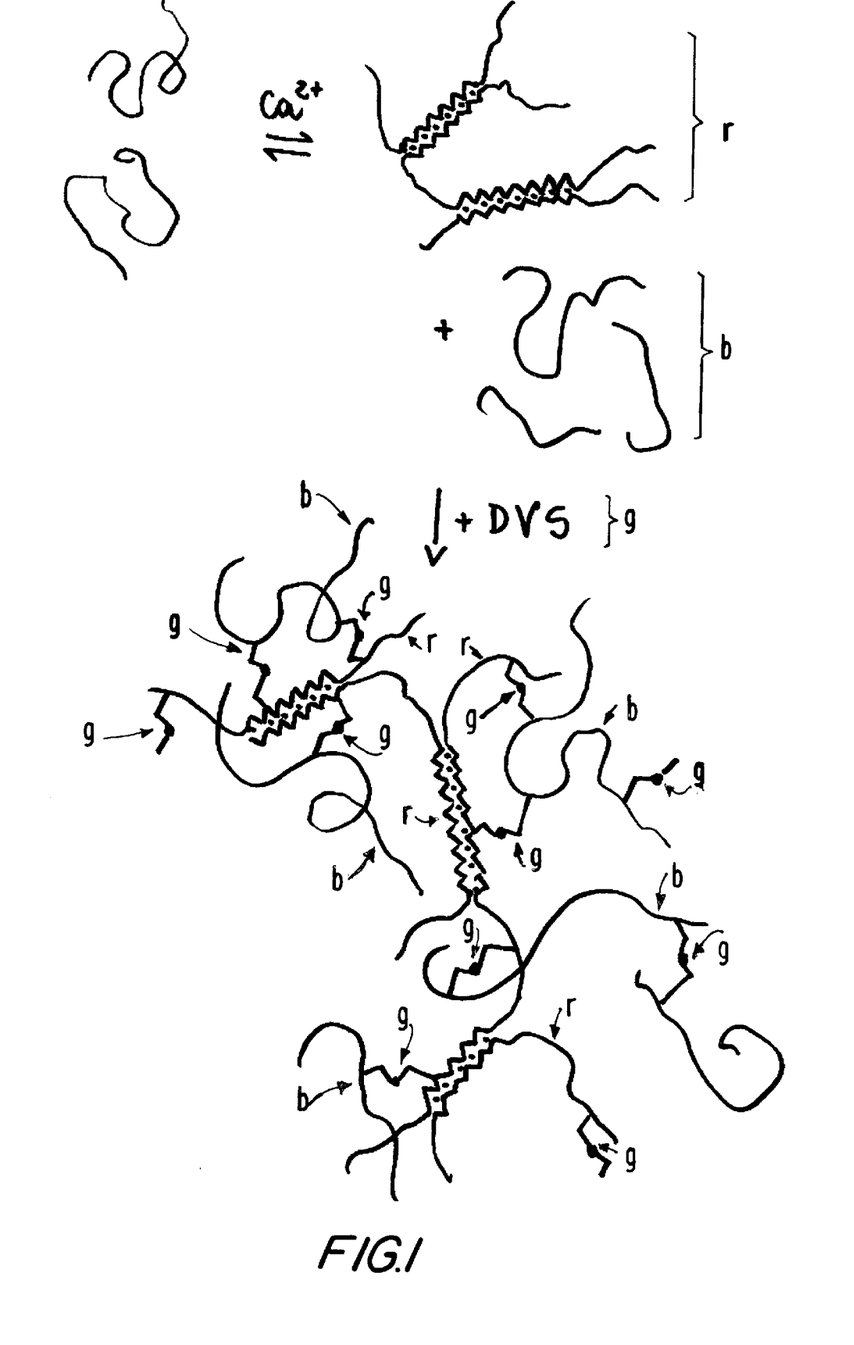
FIG. 1 shows a schematic structure of Biodritin (in red—also labeled "r", coiled alginate chains that associate with calcium ions to form the "egg-box" structures, in the gel state; in blue—also labeled "b", alginate chains; green—also labeled "g", DVS molecules that cross-link CIS and alginate. The idealized picture at the bottom shows CIS molecules bound to alginate, with the "egg-box" structures characteristic of the gelled state; the cross-linking bonds have the structure —$CH_2SO_2$—$CH_2$—)
Figure 4:
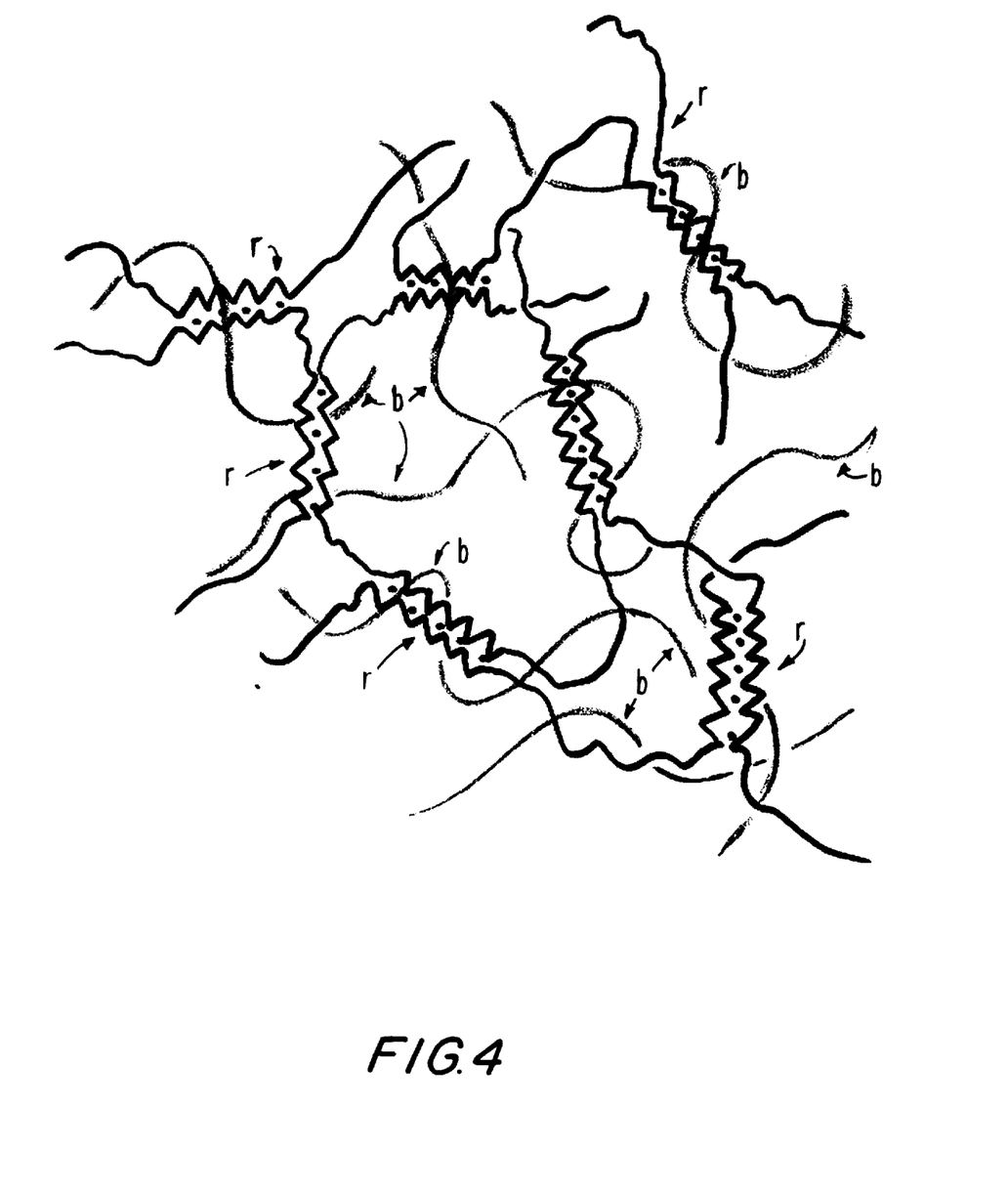
FIG. 4 is a scheme of the structure of a semi-interpenetrating polymer network formed by CIS and alginate.

A schematic representation of the complex chemical structure of biodritin is shown in FIGS. 1 and 4, respectively, for the chemically coupled and the physical gel.

The following non-limiting Examples are given by way of illustration only and are not to be considered a limitation of this invention, many apparent variations of which are possible w/o departing from the spirit or scope thereof.

EXAMPLES

Example 1—Preparation of the reactant solutions

Chondroitin sulfate: the commercial CIS used contains 70% of 4-sulfate and 30% of 6-sulfate; 2.5 g was allowed to dissolve in 25 ml 0.1 M sodium carbonate solution, to give a 100 mg/ml final concentration. In other formulations, higher concentrations of CIS are used, to give final concentrations of 150, 200 or 250 mg/ml.

Sodium alginate (5.0 g) was suspended in 45 ml of water, heated to 40° C., after which another 30 ml water were added in 10 ml portions to facilitate dissolution and decrease viscosity of the final solution. The amount of sodium alginate used corresponds to 28.3 mmoles of the unit disaccharide residue of alginate (F.Wt.=176.2).

Example 2—Partial protection of calcium binding sites

The total blockage of the calcium sites in the alginate solution would require 6.5 ml of a 4.5 M $CaCl_2$ solution, which is not practical to use. A 4.5 M calcium chloride stock solution was diluted 1:5 and 200 µl portions were added at intervals to the sodium alginate solution. During additions, and thereafter, the solution was vigorously mixed with the aid of a power mixer to completely avoid formation of gel clumps. Eight such additions, plus one, were made, in a total of 1800 µl, corresponding to 1.5 mmol of calcium ions added.

Biodritin preparations can also be made in which the calcium binding sites are blocked to a lesser extent, from 25% to 75% of that described above. This also results in soluble materials, provided the coupling with DVS is not extensive.

In applications where the s-IPN gel is prepared, protection of the calcium binding sites is not necessary, as there is no chemical reaction with the alginate component of Biodritin prior to the gel-forming step.

Example 3—DVS-Coupling Reaction

Keeping the alginate gel with protected calcium binding sites under continuous, vigorous mixing, 25 ml of the CIS solution were added, at which time the solution viscosity decreased. The solution was rapidly homogenized by the vigorous mixing and the coupling reagent, DVS, was added in 10 portions of 0.3 ml each, under continuous mixing at 2–3 min intervals.

When DVS addition was complete the mixture was kept for 2 hours in a water bath at 40° C. At the end of this interval the reaction mixture was slightly purple in color; it was removed from the water bath and left overnight at room temperature.

During the reaction steps, continuous mixing is required, which can be easily achieved with help of an electrical mixer with blades or paddles.

Example 4—Processing and Initial Purification

After reaction is complete, the mixture resembled a mousse. To each 100 ml portion of this material was added 15 ml of 1M NaCl and 5×1 ml portions of a 0.63 M EDTA solution, to remove calcium ions from the "egg-box" sites. Mixing was maintained to facilitate solubilization. A very viscous and brownish solution was finally obtained.

The solution was cooled in an ice-water bath, after which 3×100 ml portions of ice-cold ethanol were slowly added with strong mixing with spatula, to precipitate the product. A white, thread-like, copious precipitate formed; the mixture was left for one hour in the ice-water bath, after which it was centrifuged at 4° C., at 6000 rpm for a minimum of 20 minutes, in 250 ml plastic bottles.

Example 5—Blocking the remaining Active Vinyl Groups

After discarding the supernatant, the centrifuge bottle was inverted for drainage of excess liquid, the precipitate was taken and pressed between filter papers, using gloved hands. It was, then, suspended in 50 ml 1 M ethanolamine at pH 9.4, to which 1 ml 0.63 M EDTA was also added. As dissolution started, an additional 50 ml ethanolamine solution was added in two equal portions; small clumps were broken with a spatula. The solution was then stirred while heated to about 40° C., when complete solution occurred. The container was closed with parafilm and left overnight at room temperature or, alternatively, kept in a water bath at 40° C. for four hours. A golden-yellow, transparent solution resulted that was transferred to a 2 liter beaker for further treatment.

Example 6—Further Purification

The solution of the preceding step was cooled in an ice-water bath and, after 30 min, 3×100 ml portions of ice-cold ethanol were added with hefty mixing with spatula. A white, fibrous precipitate formed that sedimented easily by gravity. The suspension was kept for 1 hour in an ice-water bath, after which it was centrifuged at 6000 rpm for 20 min at 4° C., as before. The clear supernatant was discarded and the precipitate collected as in Example 4 above and dried between filter papers.

This precipitate was re-dissolved in 2×50 ml portions of water for a third ethanol precipitation. The solution was transferred to a 2 liter beaker and cooled to ice-water bath temperature. After slow addition of 3×100 ml portions of ice-cold ethanol a white, fibrous precipitate formed and the mixture was left for one hour in the ice-water bath.

The precipitate was collected after centrifugation carried out exactly as described in this Example; it was drained, pressed between filter papers and dissolved, with help of a spatula, in 100 ml water. The final solution was clear, very viscous. It was poured into petri dishes, frozen and freeze-dried.

The dry material obtained after freeze-drying was white, weighing, on the average, 5.9 g for this batch size. It was recovered as brilliant, fibrous sheets that break into flakes. The final material is completely soluble in water or 0.15 M NaCl solution. Solutions in both solvents at the levels of 10 to 30 mg/ml form gel spheres when dripped into an 1% calcium chloride solution.

Example 7—Dehydrothermal Preparation of Biodritin

Sodium alginate and CIS solutions were prepared as in Example 1 with the important modification that the solvent for each one was now water.

"Egg-box" sites were combined with calcium ions as in Example 2. CIS solution was, then, added to alginate; CIS solution can also be added before the calcium ions addition. A power mixer was used to break any clumps that could have formed at the calcium chloride addition steps. The very viscous final mixture was transferred to petri dishes, frozen and freeze-dried.

The hard, dry cake in the petri dishes was then submitted to the dehydrothermal treatment as follows: the dishes containing the cakes were placed in an electric hood maintained at 102–106° C. and kept there for 24 hours. After this time allowed for reaction, the cakes were left to cool to room temperature and further processed.

At this point an average 6.7 g of cake is obtained; it is reduced to powder and suspended into ~75 ml water to which 5–6 ml 0.63 M EDTA is added to remove calcium from the "egg-box" sites. To 100 ml of the mixture is added 10 ml of 1 M NaCl, to render it 0.1 M in NaCl, and the mixture is gently heated. Coarse lumps that would not dissolve with a spatula are removed and the mixture is centrifuged to remove insolubles. The clear supernatant is purified by ethanol precipitation as described in Example 6; a total of 3 re-precipitations are carried out, the first two after addition of 2 ml EDTA to assure complete calcium removal. After the third precipitation the cake is suspended in ~75 ml water, gently warmed to facilitate solution. The clear solution obtained is transferred to petri dishes, frozen and freeze-dried. A typical yield for such a batch is 5.6 g of final product.

The resulting powder is easily water soluble at concentrations from 10 to 40 mg/ml water or 0.1 M NaCl; the viscosity is a little less than that of equivalent concentrations of Biodritin prepared by chemical co-polymerization with DVS but microcapsules are formed when the solution is dripped into calcium chloride.

Example 8—Preparation of Biodritin-poly-L-Lysine Microcapsules

Stock solutions of Biodritin heteropolysaccharide were prepared at 10, 15, 20 mg/ml (DVS polymerized Biodritin) or 30 mg/ml (DHT Biodritin) in 0.15 M NaCl, at room temperature. Dissolution is rapid and easy. The Biodritin heteropolysaccharide solution was dripped from a syringe into a 1.1% $CaCl_2$ solution, with mild agitation, from a height of about 15 cm, forming beads. The beads were left to mature for different time intervals in the calcium chloride solution, from 5 to 40 min and were, then, processed as described by Sun et al (1984).

i- Briefly, beads are washed, successively in 0.1% CHES (cyclohexyl-ethane sulfonic acid) and 1.1% calcium chloride; they are then treated for 6 min with a 0.5% poly-Llysine solution, in order to form a capsule of Biodritin-polylysine complexes at the bead surface.

ii- The beads are, then, washed in 0.1% CHES, 1.1% calcium chloride and 0.15 M NaCl, in this order; each washing lasts 2 minutes.

iii- An outer coating of Biodritin is now applied by incubation of the capsules with a 0.03% Biodritin heteropolysaccharide solution for 4 minutes, after which the capsules are extensively washed in 0.15 M NaCl. They are stored in 0.15 M NaCl until used.

In this Example no cells were encapsulated; the microcapsules contained only Biodritin-calcium gel and the outside coatings. Pure microcapsules are used to investigate their biocompatibility in animal experiments. The external diameter of the microcapsules prepared in this Example was 4–5 mm but, using devices where a coaxial air stream flows around the syringe needle tip, much smaller microcapsules can be prepared, as is known to those versed in this field.

Example 9—Preparation of Biodritin as a s-IPN Physical gel

In this Example solutions were prepared having the following concentrations of components: solvent was 0.15 M sodium chloride; the alginate concentration was fixed at 3.0% and the CIS concentrations used were 1.5%, 3% and 6%, respectively, giving CIS/alginate ratios by weight of 0.5:1, 1:1 and 2:1. The semi-interpenetrating polymer network was prepared in bead form by dropping each of these solutions into a solution of calcium chloride at 1.1%, as described above.

Beads were formed from a 20 gauge syringe needle, at a rate of 1 ml/min (peristaltic pump); this needle was inserted into a larger one linked to an air pump so that air could be blown around the dropping needle in order to form microbeads, by fractionation of the out-flowing liquid column, that dropped into a calcium chloride solution. A typical preparation consisted of forming beads from 3 ml of each solution, received in 30 ml 0.15 M NaCl in a small beaker. Immediately thereafter the beads were transferred to a 50 ml centrifuge tube, where they were gently mixed with the calcium solution for 10 minutes. In this step the periods can vary from a few minutes to much longer ones, as 40 min, for example, depending on the extent of gelling that is desired.

After this period the beads are centrifuged off at low force (1000 rpm, 3 min), transferred to a 15 ml centrifuge tube and washed with 0.15 M NaCl. A washing sequence as described in Example 8 was applied. A poly-lysine capsule can be applied to the beads, exactly as described above.

Biodritin beads of the s-IPN type were tested for stability, without the poly-lysine capsule, by incubation for 140 hours at room temperature, in 0.15 M NaCl. Analysis of CIS and alginate leakage, made by ultra-violet spectrophotometry at 204 and 215 nm, revealed that only 6% of the total alginate in the beads leaked within the first 50 hours for the beads containing 6% CIS, about 4% alginate leaked from the beads with 3% CIS, and ca. 1% leaked from beads with 1.5% CIS, approximately the same leakage observed with alginate control beads. The leakage of CIS, on the other hand, was minimal, in all cases, less than 1%. After this period, the beads were further washed by daily exchanges of 0.15 M NaCl. The leaked amounts decreased and reached zero for all beads by the third exchange, i.e., after 72 hours. These data demonstrate that beads formed by s-IPN are stable and keep their composition after gelling. The beads formed in this Example had an average diameter of 550 µm.

Example 10—s-IPN gel formed from a mixture of DVS-CIS-cross-linked Biodritin and added CIS A biodritin solution at 2%(w/v) was prepared in 0.15 M NaCl. The biodritin powder preparation used had a DVS-crosslinked CIS content of ca 2% by weight, which was raised to 15% by addition of CIS. The final solution, thus, had a composition of 2.0% alginate and 0.3% CIS, on a w/v basis. Beads were prepared by dropping this solution into 1.1% calcium chloride solution, followed by 40 min incubation in the same solution. Additional treatment included formation of a poly-L-lysine capsule, further layered with biodritin, and washing as described in Example 8. Beads and capsules prepared in this way have identical properties to beads of similar composition prepared from alginate and CIS as in Example 9. They can be treated exactly as the beads described in the next Examples.

Example 11—Sterilization of Microcapsules

In addition to the possibility of sterilizing the Biodritin heteropolysaccharide solution, as well all other solutions used in the capsule preparation by membrane filtration before the gelation step, Biodritin microcapsules can also be sterilized by treatment with 70% (v/v) isopropanol in 0.15 M NaCl. Thus, Biodritin microcapsules were successively treated by Isopropanol/0.15 M NaCl solution of increasing isopropanol concentrations, as follows: 25%, 50% and 70%, all by volume. The first two treatments were applied for 30 min each, to allow slow dehydration of the capsules by the increasing concentrations of isopropanol. When submitted to 70% isopropanol, the microcapsules were left for up to 4 days at room temperature.

Under these conditions, they shrunk to about one-half the initial diameter, presenting wrinkles on the surface. When re-hydrated 4 days later, by decreasing concentrations of isopropanol, in the reverse order, as above, until 0.15 M NaCl was attained, they recovered the original spherical form, without shape deformations, breaks or peeling of the outer layer. The surface examination was done with help of a loupe with varying degrees of magnification.

Differently from this, microcapsules prepared with alginate alone treated the same way and in parallel experiments, shrunk to ⅓ the original volume and did not recover the initial spherical shape. Most became ellipsoids of revolution, with intact surfaces showing wrinkles that did not disappear with time.

Microcapsules treated as in Examples 8 and 9 were also implanted into mice to test their biocompatibility.

Example 12—Intactness of the Outer Microcapsule Membrane (Biodritin/Poly-Lysine/Biodritin)

The preservation of the outer membrane after sterilization and re-hydration was tested by dissolving a considerable part of the gel in the interior of the microcapsules by treatment with 0.050 M sodium citrate.

Microcapsules were incubated with sodium citrate at room temperature for varying times while observed under a loupe at high magnification. Depending on the capsule size, the time course of events changes but, for a group of larger microcapsules the following results were obtained: after ~10 min, the central core was surrounded by a narrow, very transparent zone, the latter limited by the external membrane.

At 30 min observation, the solubilization of the Biodritin gel by calcium removal by citrate reached about 50% of the capsule diameter; the outer membrane was intact. Mixing the microcapsule suspension by rotation of the flask makes possible to observe the undulating movement of the intact external membrane, also indicating that it is permeable, allowing fluid to move in and out.

Lacking the support of the subjacent gel structure, dissolved by action of citrate, the membrane can be broken by strong aspiration with a pipette.

Example 13—Microcapsule Staining with Alcian Blue

Alcian Blue is a well known stain for chondroitin sulfate (Turnbull, 1993); we found that it also stains alginate, although with less intensity. Microcapsules were stained in 0.5% Alcian Blue in 2% acetic acid, for 20 min; de-staining was in 2% acetic acid, in repeated washings. Biodritin microcapsules give a deeper blue than alginate capsules, as expected. When Biodritin microcapsules prepared as in Example 8, are cut in half and stained, the interior of the capsules stains more intensively than the outside, indicating that the external membrane has an effect on the stain diffusion to the capsule interior.

Example 14—Preparation of structured "spaghetti"-like cylinders of Biodritin for cell and tissue implantation A new use of the Biodritin invention is in the preparation of structured spaghetti-like cylinders to contain cells or tissues for implantation, itself an invention to be described for the first time herein, called biodritin spaghetti. These Biodritin spaghetti are called "structured" because the thin gel cylinder that receives the name spaghetti has an interior structure formed by a string of sewing cotton line or, alternatively, of surgical suture line. The cotton line has a multitude of very fine lateral extensions, as short branches in a long caulis, that spring from the line surface and are embedded into the gel. The surgical suture does not have such branches, but they can be created by scratching the surface of the line with a knife blade, before sterilizing. These lateral extensions of the central line core provide additional area for adhesion between the gel matrix and the central core, reinforcing the structure in a way similar to the iron wires in concrete.

Structured Biodritin spaghetti are prepared as follows:
1) a sterilized cotton sewing line, size 50 or thinner is inserted into a 10 to 20 cm sterile polyethylene catheter of the desired diameter—usually size 60, but size 90 can be used with thinner lines—up to the point where the line reaches the needle, itself connected to a syringe. A surgical suture line can be used in place of the cotton line, with equivalent results. The line should extend beyond the free end of the catheter tubing for 4 to 5 cm, so that in can be handled, anchored or restrained later on in the process (see FIG. 2A).

2) A Biodritin heteropolysaccharide solution of desired concentration, between 0.5 and 3.0%, for example, in the required solvent (saline, culture medium, or Hank's medium), and containing the cell or tissue preparation desired, is introduced into the catheter tubing by syringe aspiration through the catheter, with the line in place. After a given length of the catheter is filled with the solution the catheter tip and the line extension are briefly rinsed with solvent and the set up is ready for spaghetti formation.

3) A structured spaghetti is formed as follows: the catheter filled with Biodritin heteropolysaccharide solution containing cells and connected to the syringe is quickly placed into a calcium chloride solution in a large petri dish or shallow tray and the syringe plunger is pressed, as the catheter is continuously moved forward in the calcium chloride solution. As the Biodritin heteropolysaccharide solution exits the catheter, it enters into immediate contact with calcium ions and instantly forms a cylindrical gel around the cotton line or surgical line. When all the Biodritin heteropolysaccharide solution in the catheter is expelled by the syringe, one is left with a cylindrical gel formed around the line, whose extension is dictated by the amount of Biodritin heteropolysaccharide solution originally in the catheter. At each end of the Biodritin gel there is a continuous piece of line that is now used to hold the gel cylinder during further processing.

4) The Biodritin spaghetti is now left in the calcium chloride solution for a given period of time to strengthen the gel; this period varies according to the type of gel desired, and ranges from 5 to 40 minutes. After the incubation with calcium ions the Biodritin spaghetti are treated exactly as under Example 8, to form a Biodritin-poly-L-Lysine membrane covering the spaghetti surface area. This external Biodritin/polylysine/Biodritin membrane helps to support the gel and controls permeability according to molecular size.

Figure 2A:
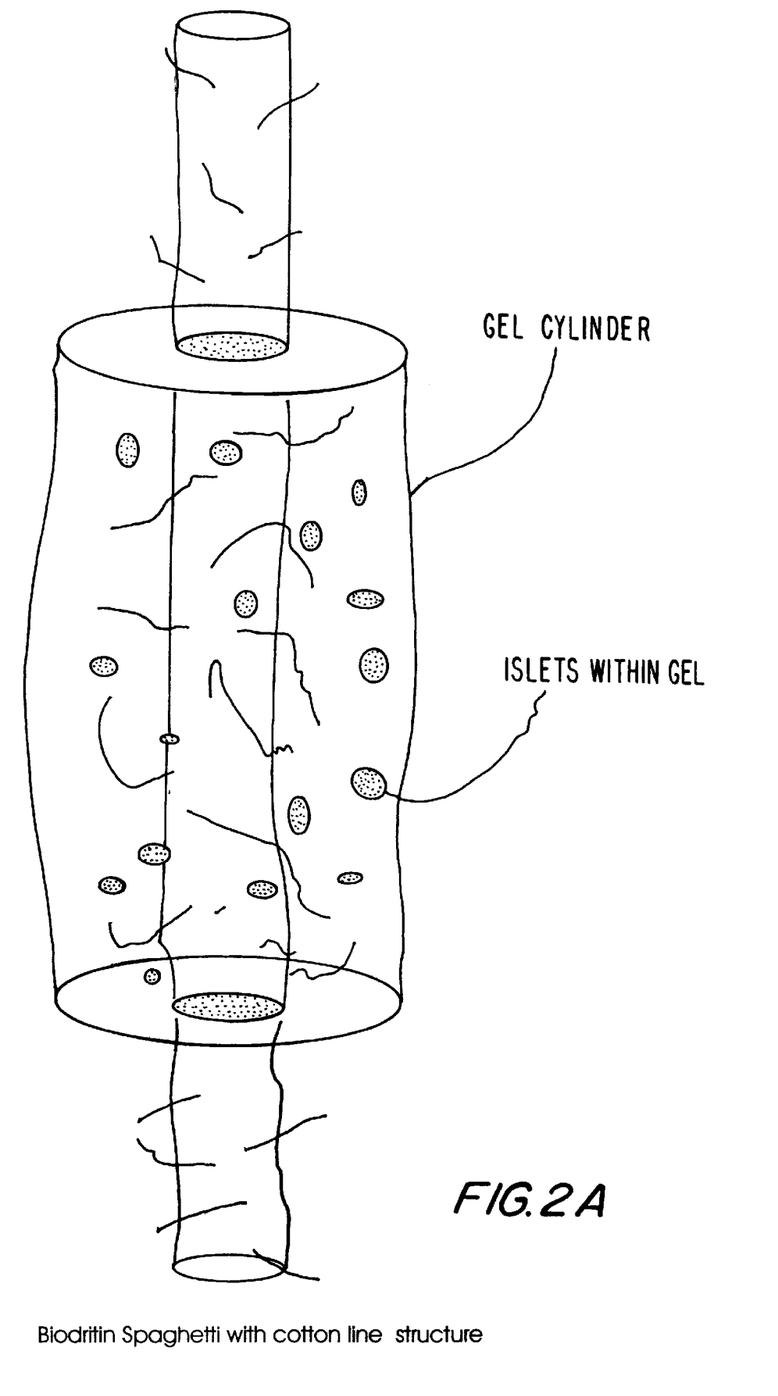
FIG. 2A shows a scheme of a Biodritin spaghetti cylinder showing the structuring cotton line, with its small lateral projections, the surrounding Biodritin gel cylinder containing islets, represented by round or oval black spots.

5) When islets of Langerhans or other cells or tissue are suspended in the Biodritin spaghetti, they distribute themselves in the double cylindrical space contained within the limits of the cotton or surgical line surface, in the inside, and the Biodritin/poly-lysine/Biodritin membrane, in the outside, as shown in FIG. 2A. The number of islets contained per unit cylindrical volume can be controlled by the islet suspension prepared originally in the Biodritin solution. The biocompatible Biodritin gel structure that forms the bulk of the spaghetti supports the islets away from each other and prevents that they clump together, thereby avoiding central necrosis in islets aggregates.

Figure 2B:
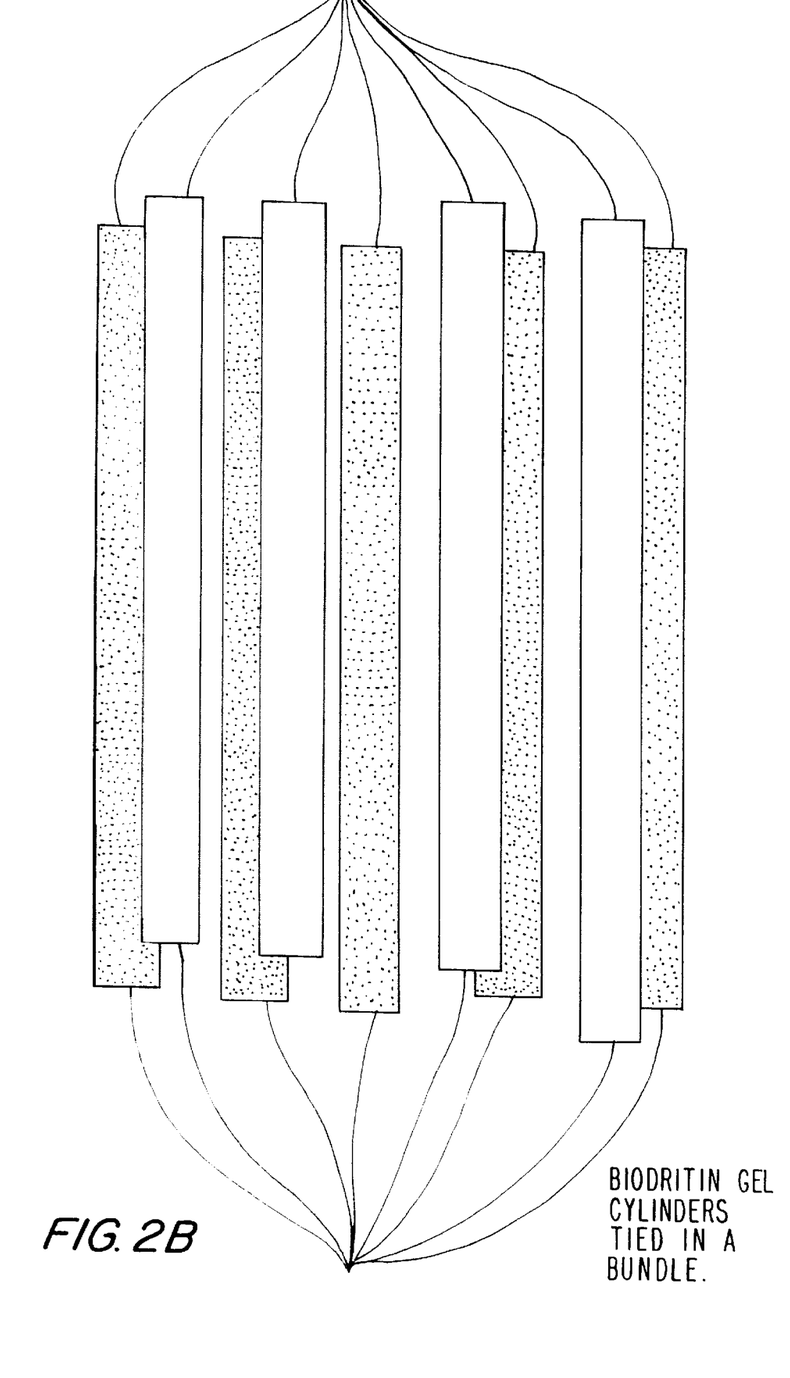
FIG. 2B shows a representation of a group of 9 Biodritin structured spaghetti tied together in a bundle.

6) The Biodritin spaghetti, with the line extensions at each end, may be implanted individually or can be tied together by the line ends before inplantation, as shown in FIG. 2B. In this way, a much larger mass of cells may be implanted, in a rather limited space, but under conditions that preserve the individual spaghetti.

Figure 3:
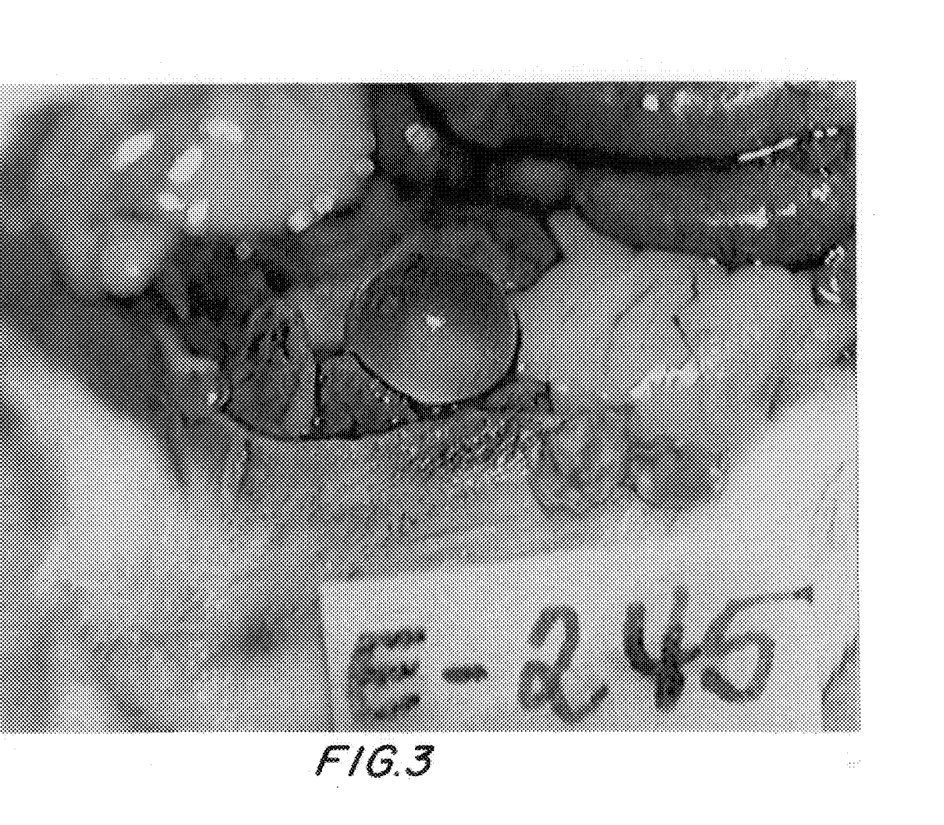
FIG. 3 is photograph of a Biodritin bead with its poly-L-lysine/Biodritin external capsule, removed from a mouse after 3 months intraperitoneal implantation (a clean and translucent surface is clearly visible)

7) Another embodiment of the present invention is that a group of Biodritin spaghetti strings with cells, tied together as in FIG. 3B, can be placed inside a porous, protective and biocompatible external cylinder initially prepared from veins or arteries of an animal or from the recipient himself. Once attached within such a biocompatible container, to form a sort of living tissue cartridge, the Biodritin spaghetti strings can be implanted into a patient. A possible and interesting alternative proposed in this invention is through the umbelical scar in such a way that, eventually, replacement cartridges may be exchanged using rather simple surgical technique.

8) Under the preparation conditions described above, a Biodritin spaghetti of gel length equal to 10 cm would have the following approximate dimensions (FIG. 4): A) gel length—100 mm; B) total internal diameter—0.76 mm; C) cotton line diameter— 0.20 mm; D) thickness of Biodritin gel cylinder (B–C)—0.50 mm; volume of Biodritin gel—42.2 $mm^3$, or 4.22 $mm^3$ per linear centimeter length.

Example 15—Animal implants of Biodritin Microcapsules: Biocompatibility

Biodritin microcapsules of 4–5 mm diameter were implanted intra-peritoneally in mice, 3 capsules per mouse, 2 mice per group, following standard surgical procedures and approved protocols.

After one week, one month and three months post-implantation periods the capsules were removed from the animals. The week-long implanted capsules were found to be free in the peritoneal cavity, clean and with no adherences; no inflammatory reaction could be observed in or around the site where they were found.

Similar results were found with the microcapsules that stayed for one month or three months intra-peritoneally in mice. The capsules showed a clean, brilliant surface, free of any adherences. As with the week-long experiments, no inflammatory reaction was noticed. FIG. 4 shows a capsule removed from a mouse after three months intraperitoneal implantation. Histological study of the preparations fully supported the conclusion: no cells were found on the beads surface after intraperitoneal implantation for eight days, one month and three months.

Thus, the biocompatibility of this novel material was established, as expected from the ubiquitousness of chondroitin sulfate in the animal kingdom and from its demonstrated inherent non-immunogenicity.

Example 16—Surgical Biodritin paint or spray for suture protection

In another embodiment of the present invention, a 0.8 to 1.5% (w/v) Biodritin heteropolysaccharide solution in saline is painted on and around a surgical suture; immediately thereafter a 1% (w/v) calcium chloride solution is briefly sprayed as a mist over the painted area. There immediately forms a Biodritin gel over the painted area that protects it from invading cells or from adhering to adjoining tissue. This has important applications in abdominal surgeries, where undesired adherences may form after surgical procedures. As an alternative mode of application, the Biodritin heteropolysaccharide solution can be sprayed over and around the suture, followed by spraying of the calcium chloride solution to form the Biodritin gel.

A third manner of Biodritin application is to mix the Biodritin heteropolysaccharide solution with an insoluble calcium salt, such as tricalcium citrate, forming an uniform suspension of the calcium salt and, immediately before application, mixing this with an aqueous solution of the δ-lactone of gluconic acid, which slowly hydrolyzes to gluconic acid, which dissolves the calcium ions from the citrate, thereby forming the Biodritin gel in situ. This formulation is called "internal gelation" and has been employed to encapsulate microbial cells by Johansen and Fink (1988). To perform this formulation the following proportions are recommended: to each 8 ml of Biodritin heteropolysaccharide solution of adequate concentration (2.5%, for example) add 1 ml of a tricalcium citrate solution (11.4 mg /ml) and, finally, 1 ml of glucono-lactone (10 mg/ml). Upon addition of the gluconolactone the solubilization of calcium oind takes place in minutes, when the gel starts forming. This is the preferred embodiment of this application.

Having thus described in detail the preferred embodiments of the present invention, it is to be understood that the invention defined by the appended claims is not to be limited by particular details set forth in the above descriptions as many apparent variations thereof are possible without departing from the spirit or scope of the present invention.

REFERENCES 1. devos, P., De Haan, B. J. and van Schilfgaarde, R. (1996) Effect of Alginate Composition on the Biocompatibility of Alginate-poly-L-Lysine microcapsules. PhD Thesis, University of Groningen, The Netherlands.

2. Aruffo, A., Stamenkovic, I., Melnick, M., Underhill, C. B. and Seed, B. (1990) CD44 is the Principal Cell Surface Receptor for Hyaluronate Cell 61, 1303–1313.

3. Rosenman, S. and St.John, T. (1993) CD-44, in Guidebook to the Extracellular Matrix and Adhesion Proteins, T. Kreis and R. Vale, Editors, Oxford University Press, p. 27–29.

4. Zimmerman, D. R. (1993) Versican, in Guidebook to the Extracelluuar Matrix and Adhesion Proteins, T. Kreis and R, Vale, Editors, Oxford University Press, Oxford, p.100–101.

5. Cole, G., Loewy,A. and Glaser, L. (1986) Neuronal Cell-Cell Adhesion depends on interactions of N-CAM with Heparin-like molecules. Nature, 320, 445–447.

6. Liao, N-S., St.John, J., McCarthy, J. B. and Furcht, L. T. and Cheung, H. T. (1988) Adhesion of Lymphoid Cells to the Carboxyl-terminal Heparin-binding Domains of Fibronectin. Exp. Cell Res. 181, 348–361.

7. Moscatelli, D. (1988) Metabolism of Receptor-bound and Matrix-bound Basic Fibroblast Growth Factor by Bovine Capillary Endothelial Cells. J. Cell. Biol. 107, 753–759.

8. Christenson, L., Dionne, K. E. and Lysach, M. (1993) Biomedical Applications of Immobilized Cells, in Fundamentals of Animal Cell Encapsulation and Immobilization, M. F. A. Goosen, editor, CRC Press, Boca Raton, p.7–41.

9. Goosen, M. F. A. (1993), editor, Fundamentals of Animal Cell Encapsulation and Immobilization, CRC Press, Boca Raton, p. 1, -326.

10. Wang, P. Y. (1991) Sustained-release implants for insulin delivery, in Biotechnology of Insulin Therapy, John C. Pickup, editor, Blackwell Scientific Publications, London, p. 42–74.

11. Howell, S. L., Ishaq, S. and Tyhurst, M. (1982) Possible use of agarose gels as encapsulating media for transplantation of islets of Langerhans. J. Physiol. 324, 20p–21p.

12. Tze, W. J. and Tai, J. (1982) Biocompatibility and immunological studies of microencapsulation with cross-linked alginate capsules. Transplantation 33, 563–564.

13. Young, D. V., Dobbels, S., King, L., Deer, F. and Gillies, S. D. (1989) Inverted microcarriers: using microencapsulation to grow anchorage-dependent cells in suspension. Biopharm 2, 34, 36, 38, 40–46.

14. Murphy, G. F., Orgill, D. P. and Yannas, I. (1990) Partial dermal regeneration is induced by biodegradable collagen-glycosaminoglycan grafts. Laboratory Invest. 63, 305–313.

15. Yannas, I., Orgill, D. P. and Murphy, G. F. (1990) Chemical analogs of the extracellular matrix. Cell-matrix interactions. Polym. Mater. Sci. Eng. 62, 801–803.

16. Slivka, S. R., Landeen, L. K., Zeigler, F., Zimber, M. P. and Bartel, R. L. (1993) Characterization, barrier function and drug metabolism of an in vitro skin model. J. Invest. Dermatol. 100, 40–46.

17. Hirschman, A. and Dziewiatkowski, D. D. (1966) Protein-polysaccharide loss during endochondral ossification: immunochemical evidence. Science 154, 393–395.

18. Loewi, G. and Muir, H. (1965) The antigenicity of chondromucoprotein. Immunology 9, 119–127.

19. Lim, F. and Sun, A. M. (1980) Microencapsulated islets as a bioartificial pancreas. Science 210, 908.

20. Stevenson, W. T. K. and Sefton, M. V. (1993) Development of polyacrylate microcapsules, in Fundamentals of Animal Cell Encapsulation and Immobilization, M. A. F. Goosen, Editor, CRC Press, Ch.7, p.143–181.

21. Jindal, R. and Gray, D. (1994) Preservation and storage of pancreatic islets. Transplantation 57, 317–321.

22. Rodriguez Rilo, H. L., Carroll, P. B., Zeng, Y. J., Fontes, P., Demetris, J. and Ricordi, C. (1994) Acceleration of chronic failure of intrahepatic canine islet autografts by a short course of prednisone. Transplantation 57, 181–187.

23. Lee, Y. C. and Lee, R. T. (1994) Neoglycoconjugates. Preparation and Applications, Academic Press 24. Magnusson, G., Chernyak, A. Ya., Kihlberg, Y. and Kononov, L. O. (1994) Synthesis of Neoglycoconjugates, Ch.3, p.53–143, in Lee and Lee (1994), loc.cit 25. Johansen, A. and Flink, J. M. (1986) A New Principle for Immobilized Yeast Reactors based on Internal Gelation of Alginate. Biotechnol Lett, 8, 121–126.

26. LaPorte, R. J. (1997) Hydrophilic Polymer Coatings for Medical Devices, Technomic Publishing Co,Inc, Lancaster, Ch.2, p.19–55.

What we claim is:

1. A composition comprising at least one glycosaminoglycan, which glycosaminoglycan is selected from the group consisting of chondroitin sulfate-4 and chondroitin sulfate-6, and at least one alginate, wherein:

the at least one glycosaminoglycan and the alginate are covalently bound; or the at least one glycosaminoglycan and/or the alginate are cross-linked or polymerized and the at least one glycosaminoglycan and the alginate are covalently bound by means of a coupling reaction involving a linker molecule.

2. The composition of claim 1 wherein the linker molecule is a sulfone.

3. The composition of claim 2 wherein the sulfone is divinyl sulfone.

4. The composition of claim 1 wherein the at least one glycosaminoglycan and/or the alginate are cross-linked or polymerized and the at least one glycosaminoglycan and the alginate are covalently bound by means of a coupling reaction involving a linker molecule.

5. The composition of claim 4 wherein the alginate is cross-linked or polymerized by an inorganic salt.

6. The composition of claim 5 wherein the inorganic salt is a calcium salt.

7. The composition of claim 4 wherein the at least one glycosaminoglycan and the alginate are covalently bound by means of a coupling reaction involving a linker molecule.

8. The composition of claim 7 wherein the linker molecule is a sulfone.

9. The composition of claim 8 wherein the sulfone is divinyl sulfone.

10. The composition of claim 4 which is formed by performing the covalent bonding prior to cross-linking or polymerizing.

11. The composition of claim 4 which is formed by performing the cross-linking or polymerizing prior to performing the covalent bonding.

12. The composition of claim 1 wherein the alginate forms a gel in the presence of an inorganic ion.

13. The composition of claim 12 wherein the inorganic ion is a calcium ion.

14. The composition of claim 13 wherein the alginate is sodium alginate.

15. A gel comprising a composition of claim 1.

16. The gel of claim 15 wherein the gel is a semi-interpenetrating polymer network.

17. The gel of claim 15 wherein the gel is an infinite gel by the presence of calcium ions.

18. A sol comprising a composition of claim 1.

19. A paint or spray comprising a composition of claim 1.

20. A matrix comprising a composition of claim 1.

21. The matrix of claim 20 comprised of beads.

22. The matrix of claim 20 comprised of a cylindrical structure having the composition surrounding an interior line optionally having lateral extensions protruding therefrom.

23. The matrix of claim 20 comprised of gel microcapsules.

24. A formulation having an adjustable viscosity comprising a composition as claimed in claim 1 and calcium ions, wherein the viscosity is adjustable by varying the composition and/or calcium ion concentration(s).

25. A method for preparing a composition as claimed in claim 1 comprising reacting the at least one glycosaminoglycan and the alginate with a linker molecule.

26. The method of claim 25 wherein the linker molecule is a sulfone and the reaction is carried out in an alkaline medium.

27. The method of claim 26 wherein the sulfone is divinyl sulfone.

28. The method of claim 25 further comprising protecting calcium binding sites of the alginate prior to reacting.

29. The method of claim 25 further comprising eliminating remaining active vinyl groups in the composition by reacting with an alkanolamine at an alkaline pH.

30. The method of claim 29 wherein the alkanolamine is ethanolamine.

31. A method for preparing a composition as claimed in claim 1 comprising admixing the at least one glycosaminoglycan and the at least one alginate, and contacting the mixture with an inorganic ion, and covalently bonding the at least one glycosaminoglycan and the at least one alginate either prior to contacting the mixture with the inorganic ion or after contacting the mixture with the inorganic ion.

32. The method of claim 31 wherein the inorganic ion is calcium.

33. The method of claim 31 further comprising purifying the composition by contacting the composition with a compound which binds to or complexes or conjugates with the inorganic ion.

34. The method of claim 33 further comprising precipitating the composition from an alcohol solution.

35. The method of claim 34 wherein the alcohol is ethanol.

36. The method of claim 33 wherein the inorganic ion is calcium and the compound is EDTA.

37. A method for preparing a composition of claim 1 comprising subjecting a dry cake comprising the at least one glycosaminoglycan and the at least one alginate to a dehydrothermal reaction.

38. The method of claim 37 further comprising preparing the dry cake by freeze-drying a solution comprising the at least one glycosaminoglycan and the at least one alginate.

39. The method of claim 37 further comprising protecting calcium binding sites by adding calcium ions.

40. The method of claim 39 further comprising removal of calcium from calcium binding sites by contacting the composition with a compound which binds to or complexes or conjugates with calcium.

41. The method of claim 40 wherein the compound is EDTA.

42. The method of claim 40 further comprising precipitating the composition from an alcohol solution.

43. The method of claim 42 wherein the alcohol is ethanol.

44. A method for preparing the sol of claim 18 comprising contacting the composition with a sodium salt.

45. The method of claim 44 wherein the sodium salt is a citrate salt or ethylene-diamine-tetraacetic acid salt.

46. A method for preparing a gel microcapsule of claim 23 comprising dripping a solution comprising the composition into an inorganic ion solution.

47. The method of claim 46 wherein the inorganic ion solution is a calcium ion solution.

48. The method of claim 47 wherein the calcium ion solution is a calcium chloride solution.

49. The gel of claim 15 in the form of a shaped object.

50. A method for preparing the gel of claim 49 comprising fashioning the composition into the form of the shaped object and contacting the composition with a gelling agent.

51. The method of claim 50 wherein the gelling agent comprises a calcium ion and the composition is in solution when fashioned into the form of the shaped object.

52. A method for preparing the matrix of claim 22 comprising co-extruding the line, composition and an inorganic ion solution.

53. The method of claim 52 wherein the inorganic ion solution comprises a calcium ion solution.

54. The method of claim 52 further comprising forming an outer layer of poly-lysine/composition over the cylindrical structure.

55. The matrix of claim 20 further comprising cells within the composition.

56. The matrix of claim 21 further comprising cells within the beads.

57. The matrix of claim 22 further comprising cells within the cylindrical structure.

58. The matrix of claim 23 further comprising cells within the gel microcapsule.

59. The matrix of any one of claims 55 to 58 wherein the cells are pancreas islets of Langerhans.

60. A device comprising at least two matrices of claim 57 tied together at each end.

61. The device of claim 60 further comprising an additional biocompatible material surrounding the cylindrical structure for protection from mechanical strains.

62. The device of claim 60 wherein the cells are pancreas islets of Langerhans.

\* \* \* \* \*